United States Patent [19]

Kampfer et al.

[11] 4,308,390

[45] Dec. 29, 1981

[54] PROCESS FOR THE PRODUCTION OF SULPHOALKYL QUATERNARY SALTS

[75] Inventors: Helmut Kampfer; Max Glass, both of Cologne, Fed. Rep. of Germany

[73] Assignee: Agfa-Gevaert Aktiengesellschaft, Leverkusen, Fed. Rep. of Germany

[21] Appl. No.: 127,743

[22] Filed: Mar. 6, 1980

[30] Foreign Application Priority Data

Mar. 8, 1979 [DE] Fed. Rep. of Germany ....... 2909200

[51] Int. Cl.$^3$ ............................................ C07D 277/62
[52] U.S. Cl. .................................... 548/169; 542/472; 546/136; 546/153; 546/334; 548/121; 548/143; 548/217
[58] Field of Search ................ 542/472; 546/334, 153, 546/136; 548/143, 121, 169, 217

[56] References Cited

FOREIGN PATENT DOCUMENTS

2423482 12/1974 Fed. Rep. of Germany .
1419218 12/1975 United Kingdom .

OTHER PUBLICATIONS

Mees et al., The Theory of Photographic Process, pp. 202–221 (1966) 3rd ed. equivalent pages from 4th ed., Macmilan Pub. Co. 1977 on spectral sensitizers of cyanine dyes and merocyanine dye classes.
Furukawa et al., Chem. Abst. vol. 52, abstract bridging cols. 10917 to 10918 (1958).

*Primary Examiner*—John D. Randolph
*Attorney, Agent, or Firm*—Connolly and Hutz

[57] ABSTRACT

Sulphoalkyl and sulphoalkenyl quaternary salts of heterocyclic nitrogen compounds are prepared by reacting heterocyclic compounds containing a tertiary ring nitrogen atom at an elevated temperature with an O-sulphoalkyl or O-sulphoalkenylisourea compound.

3 Claims, No Drawings

PROCESS FOR THE PRODUCTION OF SULPHOALKYL QUATERNARY SALTS

The present invention relates to a process for the production of sulphoalkyl quaternary salts of tertiary amines, especially of heterocyclic bases containing nitrogen.

These kinds of quaternary salts, which contain positively charged groups and negatively charged groups inter-connected by covalent bonds, are also known as betaines. They play an important part in a number of commercial processes. In these processes the betaines are either used directly as such, e.g. in electro plating, or are used as intermediates and further reacted. When sulphoalkyl betaines are used as intermediates, it is often advantageous not to isolate them after they have been prepared, but to carry out the further reaction as a stage subsequent to the process of their production. As intermediates, the sulphoalkyl betaines play an important role, for example, in the synthesis of the polymethine dyes which are used as spectral sensitising dyes for materials which are sensitive to light, especially for photographic silver halide emulsions. The present invention therefore further relates to the conversion of heterocyclic bases via the sulphoalkyl quaternary salts into polymethine dyes.

Processes for the production of sulphoalkyl quaternary salts of tertiary amines have been known for a long time. The tertiary base is reacted with a sulphoalkylating agent, usually at a raised temperature. The following are examples of sulphoalkylating agents:

Haloalkane sulphonic acids, e.g. 2-bromoethanesulphonic acid as described in U.S. Pat. No. 2,503,776; sodium iodoethanesulphonate as described in Belgian Pat. No. 669,308; sodium iodobutane sulphonate as described in U.S. Pat. No. 2,912,329 or 3-chloro-2-hydroxypropane sulphonic acid as described in German Auslegeschrift No. 1,177,482. Disadvantages of these sulphoalkylating agents are the high reaction temperatures which are necessary and the excess of a tertiary base which is necessary in the use of the free sulphonic acids, for absorbing the hydrogen halide which is produced in the reaction. Known sulphoalkylating agents also include sultones: propane sultone, butane sultone and isopentane sultone are described in German Pat. No. 929,080; propene sultone is described in German Auslegescrift No. 1,447,579 and 2-chloropropane sultone is described in GB Pat. No. 1,090,626. A disadvantage of the sultones is partly their great carcinogenic potential, which makes their use a safety hazard for the people who work with them. This is discussed by H. Druckrey et al. Naturwiss. 55, (1968) 449 and Z. Krebsforschung 75, (1970) 69.

Another process for the production of sulphoalkyl quaternary salts from heterocyclic bases is described in Research Disclosure No. 16 374 (November 1977). According to this process, hydroxy alkane sulphonic acid and hydroxy alkene sulphonic acid are used for sulphoalkyl quaternisation. This process also requires comparatively high temperatures presumably because in the reaction water is released and has to be removed from the reaction medium. Because of the particular reaction conditions (high temperatures, acidic medium, the sulphoalkyl quaternary salts from certain particularly sensitive nitrogen bases (e.g. oxazole bases and thiadiazole bases) and also from bases containing acid-sensitive groups, for example alkoxy groups and nitrile groups, can be obtained by this process only with difficulty in the required high yield. Moreover, under these conditions, 2-methylthiothiadiazole bases tend to a displacement on quaternisation which has the effect that the sulphoalkyl radical replaces the methyl group in the 2-position and gives rise to difficulties during the subsequent condensation reaction to form the cyanine dye.

For these reasons, the object of the present invention was to provide a process for the production of sulphoalkyl quaternary salts, which does not have the disadvantages mentioned above.

A process has now been found for the production of sulphoalkyl quaternary salts and sulphoalkenyl quaternary salts of tertiary amines and more preferably of heterocyclic bases containing at least one nitrogen atom, in which the teriary amine is reacted with an O-sulphoalkyl isourea compound or an O-sulphoalkenyl isourea compound. The reaction generally takes place at elevated temperature, e.g. at a temperature of between 80° and 200° C., preferably at a temperature of between 110° and 160° C.

In general the reaction takes place very smoothly within the last named temperature range. However, it can also be carried out outside this temperature range depending to a certain extent on the nature of the solvent used.

Suitably tertiary amines include in principle all quaternisable derivatives of ammonia ($NH_3$), in which each of the three hydrogen atoms is substituted, e.g. by a carbon atom of an alkyl or aryl radical or by a carbon atom or a heteroatom of a heterocyclic ring, in which case, it is preferred that the nitrogen atom of the tertiary amine forms part of the heterocyclic ring. Particularly preferred heterocyclic bases include those of the general formula I

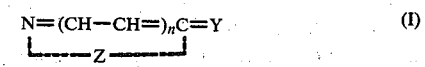

in which

Z represents the members required to complete a heterocyclic group comprising at least one 5- or 6-membered heterocyclic ring: the heterocyclic group may have benzene, naphthalene or further heterocyclic rings condensed to the 5- or 6-membered heterocyclic ring mentioned above and the heterocyclic group may carry further substituents such as alkyl, aralkyl or aryl groups, alkoxycarbonyl groups, acyl groups, cyano groups, halogen atoms, alkoxy groups, alkylthio groups, mercapto groups and sulpho groups. Suitable heterocyclic rings are those which are known from the cyanine dyes, for example:

Pyrroline (e.g. 4,4-dimethyl-pyrroline); oxazoline (e.g. 4,4-dimethyloxazoline); thiazoline (e.g. 5-methylthiazoline); selenazoline; indoline (e.g. 3,3-dimethylindoline, 3,3-dimethyl-5-methoxyindoline and 3,3-dimethyl-5-diethylamino-indoline); benzimidazole (e.g. 1-ethyl-5-trifluormethylbenzimidazole, 1-methyl-5-chlorobenzimidazole, 1-ethyl-5,6-dichlorobenzimidazole, 1-ethyl-5-cyanobenzimidazole, 1-methyl-5-carbethoxybenzimidazole, 1-ethyl-5-acetylbenzimidazole, 1-methyl-benzimidazole-5-sulphonic acid pyrrolidide, 1-ethyl-benzimidazole-5-sulphonic acid dimethylamide, 1-ethyl-5-phenylthiobenzimidazole, 1-methyl-5-methylthiobenzimidazole and 1-methyl-5-chloro-6-methylthiobenzimidazole); oxazole (e.g. 4-methyloxazole, 4,5-diphenyloxazole, 4-methyl-5-carbethoxyoxazole, benzoxazole, 5-chlorobenzoxazole, 5-phenylbenzoxazole, 6-methoxybenzoxazole, 5-methyl-6-methoxybenzoxazole, 5-bromobenzoxazole, 5-iodobenzoxazole, naphtho [2,1-d]oxazole, naptho [1,2-d]oxazole, naptho-[2,3-d]oxazole, 4,5,6,7-tetrahydrobenzoxazole, benzofuro[2,3-f]benzoxazole; thiazole (e.g. 4-methyl-thiazole, 4-phenylthiazole and 4-methyl-thiazole-5-acrylic acid ether ester, benzothiazole, 5-methylbenzothiazole, 6-methylbenzothiazole, 5-chlorobenzothiazole, 5-methoxybenzothiazole, 6-methoxy-benzothiazole, 5,6-dimethylbenzothiazole, 5,6-dimethoxy-benzothiazole, 5-methyl-6-methoxybenzothiazole, 5-brombenzothiazole, 5-phenylbenzothiazole, 6-methylthiobenzothiazole, 6-dimethylaminobenzothiazole, 5-chloro-6-methoxybenzothiazole, 5,6-methylendioxybenzothiazole, 6-β-cyano ethoxybenzthiazole, 5-carbomethoxybenzothiazole, 5-nitro-benzothiazole, 5-phenylthiobenzothiazole, 5-thienyl-benzothiazole, 6-hydroxybenzothiazole, 4,5,6,7-tetrahydrobenzothiazole, 4-oxo-4,5,6,7-tetrahydrobenzothiazole, naphtho[2,1-d]thiazole, naphtho[1,2-d]thiazole, 4,5-dihydronaptho[1,2-d]thiazole, 5-methoxynaphtho[1,2-d]thiazole and 5,7,8-trimethoxynaphtho[1,2-d]thiazole; selenazole (e.g. benzoselenazole, 5-methylbenzoselenazole, 5,6-dimethylbenzoselenazole, 5-methoxybenzoselenazole, 5-methyl-6-methoxybenzoselenazole, 5,6-dimethoxy-benzoselenazole, 5,6methylendioxybenzoselenazole, 6-methyl-benzoselenazole and naphtho[1,2-d]selenazole); 1,3,4-oxadiazole (e.g. 5-methyl-1,3,4-oxadiazole and 5-phenyl-1,3,4-oxadiazole); 1,3,4-thiadiazole (e.g. 5-methyl-1,3,4-thiadiazole, 2,5-bis-methylthio-1,3,4-thiadiazole, 5-benzylthio-1,3,4-thiadiazole, 2-mercapto-5-methylthio-1,3,4-thiadiazole and 5-carbethoxymethylthio-1,3,4-thiadiazole); pyridine (e.g. 2-methylpyridine and 4-methylpyridine); pyrimidine (e.g. 2-methyl-4-methylthiopyrimidine); quinoline (e.g. 6-methylquinoline, 6-methoxyquinoline, 8-chloroquinoline, 6-fluoroquinoline, 5,6-benzoquinoline, 5,6-benzoquinoline and 6,7-benzoquinoline) and imidazo[4,5-b] quinoxaline;

n=0 or 1

Y represents hydrogen; a halogen atom; a saturated or olefinically unsaturated aliphatic hydrocarbon group, preferably containing up to 6 carbon atoms, which may be substituted, e.g. methyl, ethyl, allyl, cyanoalkyl, halo alkyl or alkoxyalkyl; an alkoxy group, e.g. carboxyalkoxy; an alkylthio group, e.g. carboxyalkylthio, sulphoalkylthio or carbalkoxyalkylthio, or a mercapto group.

Y may for example represent a polymethine chain with 1, 3 or 5 methine groups, at the end of which there is an N-alkylated heterocyclic base mostly attached at the 2-position, as is known in the chemistry of cyanine dyes. Reference is made here to F. M. Hamer, "The Cyanine Dyes and Related Compounds," (1964), Interscience Publishers John Wiley and Sons. Compounds of Formula I, in which Y is defined as above are described as "dequaternised cyanine dyes." When such dequaternised cyanine dyes are reacted in the process of the present invention, the direct products of the process are suitable as sensitising dyes without further reaction.

Suitable O-sulphoalkyl isourea compounds and O-sulphoalkenyl isourea compounds are in particular those of the general formula (II):

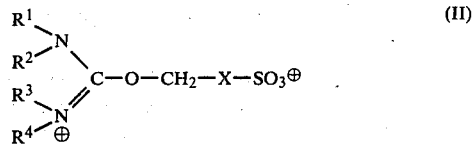

in which

X represents a saturated or olefinically unsaturated bivalent aliphatic hydrocarbon radical preferably containing up to 7 carbon atoms which may be substituted. This hydrocarbon radical may be substituted, for example, by hydroxyl, halogen, alkoxy or cyano;

$R^1$, $R^2$, $R^3$ and $R^4$ which may be the same or different, represent hydrogen, a saturated or unsaturated aliphatic hydrocarbon group, or a cycloalkyl group or any two of the substituents $R^1$, $R^2$, $R^3$ and $R^4$ may represent the atoms required to complete a 5- or 6-membered heterocyclic ring containing at least one nitrogen atom, or $R^1$ and/or $R^3$ may represent aryl if the other radical attached to the same nitrogen atom ($R^2$, $R^4$) is hydrogen.

Examples of X are the following groups:

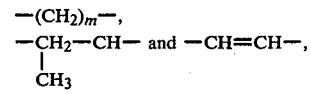

in which m represents an integer of from 1 to 3.

Alkyl groups which contain up to 4 carbon atoms are the preferred examples of the groups $R^1$, $R^2$, $R^3$ and $R^4$, such as methyl, ethyl, n-propyl and iso-propyl; these radicals may be further substituted, e.g. with aryl. Other examples include cyclohexyl and phenyl.

The reactions are generally carried out without the use of a solvent, but they can also be performed in the presence of a suitable solvent. Suitable solvents include all solvents which are inert in the reaction according to the invention, and which have a high dissolving power for the reaction components, for example phenol, m-cresol, dimethylformamide, N-methylpyrrolidone, toluene, m-xylene, chlorobenzene and anisole.

The sulphobetaines of the tertiary amines produced according to the process of the invention, are preferably those of the following formula (III)

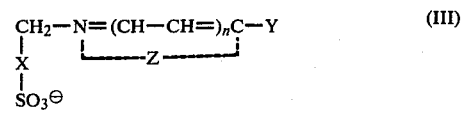

in which n, X, Y and Z have the meanings which have already been defined. The compounds have a wide range of uses. For example they are suitable as conducting salts in electroplating. Furthermore, when in the quaternary salts produced by the process according to the invention Y represents a suitable group, for example, as has already been mentioned, a methine chain with 1, 3 or 5 methine groups, on the end of which there is a N-alkylated heterocyclic base, the compound is a cyanine dye. Compounds of this kind are known and can be used without further processing in the spectral sensitisation of light sensitive silver halide emulsions. However, the compounds which are produced directly by the process according to the invention are also useful as intermediates for the synthesis of polymethine dyes. So, for example, the sulphoalkyl or sulphoalkenyl quaternary salts of heterocyclic bases which are produced by the process according to the invention are preferably not isolated, but after the quaternisation reaction is completed they are reacted without a further purification operation in a known way into polymethine dyes. In the monograph of F. M. Hamer, "The Cyanine Dyes and Related Compounds" which has already been mentioned, many cyanine dyes are described, which are derived from many different heterocyclic bases. Cyanine dyes with sulphoalkyl groups have proved to be particularly favourable for a number of reasons, especially because of their low residual dyeing.

The isourea compounds used according to the invention can be produced by known processes or rather by processes analogous to known processes. Thus, O-sulphopropyl isourea, according to K. Furakawa et al [Kogyo Kagaku Zasshi 59, 1028 (1956)] can be obtained by the reaction of urea with propane sultone. The corresponding O-sulphopropyl-N,N'-diethyl isourea is obtained according to German Offenlegungsschrift No. 2,423,482 by the analogous conversion of N,N'-diethylurea.

Instead of propane sultone, other sultones may be used e.g. n-butane sultone, isobutane sultone or propene sultone. Instead of urea or N,N'-diethylurea, other ureas, which are substituted from one to four times, can be sulphoalkylated at the oxygen atom. Ureas which are substituted four times, and in which two radicals consist of aryl groups, do not react any further. Another process for the production of isourea compounds according to the invention consists in the addition which is known per se of hydroxyl compounds to carbodiimide. Reference is made to Houben-Weyl, Methöden der Organischen Chemie VIII, S. 170; or E. Schmidt, F. Moosmüller, Liebigs Ann. 597, 235 (1955). As hydroxyl compounds, the corresponding hydroxy alkane or hydroxyalkene sulphonic acids are used here, for example 3-hydroxy-propane-1-sulphonic acid; 4-hydroxybutane-1-sulphonic acid; 4-hydroxybutane-2-sulphonic acid or 3-hydroxy-prop-1-en-1-sulphonic acid.

The hydroxy alkane or hydroxy alkene sulphonic acids, and processes for their production are known. They can for example be produced by the reaction of a halo substituted alcohol with an alkali metal sulphite or by the addition of bisulphite or $SO_2$ to a corresponding unsaturated alcohol or rather to a corresponding unsaturated aldehyde, followed by reduction. Thus, 3-hydroxy-1-propane sulphonic acid is produced from allyl alcohol by the addition of sodium bisulphite [J. H. Helberger, Liebigs Ann. Chem. 588, 71 (1974)]. 3-Hydroxy-2-methyl-1-propane sulphonic acid is produced by the addition of bisulphite to methacrolein, followed by reduction with $H_2$/Raney-Ni [C. W. Smith et al., J. Amer,chem.Soc. 75, 748 (1953)]. Analogous to this, 4-hydroxy-2-butane sulphonic acid can also be produced from crotonaldehyde [G. Haubner, Mh. Chemie 12, 541 (1891)]. 4-hydroxy-1-butane sulphonic acid can be obtained by the reaction of 4-chloro-n-butanol with sulphite [J. H. Helberger, H. Lantermann, Liebigs Ann. Chem. 586, 161 (1954)]. 3-hydroxy-1-propene sulphonic acid can be obtained by the addition of bisulphite to propargyl alcohol as a mixture of the cis- and trans-isomers as described in German Auslegeschrift No. 1,146,870.

The isourea compounds of the general formula (II), which are used in the production process of the present invention, can be thought of as internal isouronium salts, although in cases where at least one of the radicals $R^1$ to $R^4$ represents hydrogen, the compound can also be present in the tautomeric sulphonic acid form, the equilibrium being between the formulae:

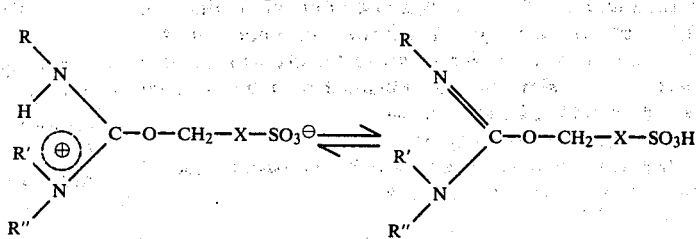

Examples of the isourea compounds used according to the invention are given below:

Compound 1: Anhydro-O-[3-sulphopropyl]-isouronium hydroxide, Mp. 184°–187° C.

Compound 2: Anhydro-O-[3-sulphopropyl]-N-methylisouronium hydroxide, Mp. 138°–144° C.

Compound 3: Anhydro-O-[3-sulphopropyl]-N,N'-dimethylisouronium hydroxide, Mp. 175°–177° C.

Compound 4: Anhydro-O-[3-sulphopropyl]-N,N,N',N'-tetramethyl-isouronium hydroxide.

Compound 5: Anhydro-O-[3-sulphopropyl]-N,N'-diethylisouronium hydroxide, Mp. 162°–163° C.

Compound 6: Anhydro-O-[3-sulphopropyl]-N-phenyl-isouronium hydroxide, Mp. 168°–170° C.

Compound 7: Anhydro-O-[3-sulphopropyl]-N,N'-diphenylisouronium hydroxide, Mp. 244°–248° C.

Compound 8: Anhydro-O-[3-sulphopropyl]-N,N'-ethyleneisouronium hydroxide, decomposes at 165° C.

Compound 9: Anhydro-O-[4-sulphobutyl]-isouronium hydroxide.

Compound 10: Anhydro-O-[3-sulphobutyl]-N,N'-dimethylisouronium hydroxide, Mp. 155°–156° C.

Compound 11: Anhydro-O-[3-sulphoprop-1-enyl]-N,N'-dimethyl-isouronium hydroxide.

Compound 12: Anhydro-O-[3-sulphopropyl]-N,N'-dicyclohexyl-isouronium hydroxide.

Compound 13: Anhydro-O-[3-sulphopropyl]-N,N'-diisopropyl-isouronium hydroxide.

Compound 14: Anhydro-O-[3-sulphopropyl]-N-benzyl-N'-methyl-isouronium hydroxide.

Compound 15: Anhydro-O-[3-sulphobutyl]-isouronium hydroxide, Mp. 210°–212° C.

The process according to the invention for the production of sulphoalkyl and sulphoalkenyl quaternary salts is explained in more detail in the following examples:

The process according to the invention provides the desired sulphoalkyl or sulphoalkenyl quaternary salts in a controlled reaction, under mild conditions. Because the reaction temperatures are lower compared to other processes and because the quaternisation agents which are used according to the invention react in a practically neutral way, more sensitive bases, especially nitrogen bases which are sensitive to acid such as oxazole bases, thiadiazole bases, alkoxy substituted bases and cyano substituted bases, can be easily and controllably quaternised. The process is also suitable for the quaternisation of 2-methylthioazole bases, which quaternisation proceeds substantially in the absence of the requaternisation, which otherwise occurs very easily.

EXAMPLE 1

Anhydro-2,5,6-trimethyl-3-[3-sulphopropyl]-benzothiazolium hydroxide, Mp. 288° C.

(a) 1/100 mol of 2,5,6-trimethylbenzothiazole is mixed with 2 ml of m-cresol and after the addition of 1/100 mol of Compound 1, is heated for 3 hours at 140° C. The melt obtained is then ground finely with acetone and the crystalline product obtained is suction-filtered and recrystallised from ethanol.

Yield: 53% of the theory.

(b) Analogous to (a), 0.01 mol of the base is reacted with 0.01 mol of Compound 3.

Yield: 73%.

(c) Analoguous to (a) using Compound 8 instead of Compound 1, in the presence of dimethylsulphoxide.

Yield: 50%.

(d) Analogous to (a) using Compound 8 instead of Compound 1 and 2 g phenol instead of m-cresol, with heating for 2 hours at 140° C. Propanol is used for working up the product.

Yield: 80%.

(e) Analogous to (a) using Compound 5 instead of Compound 1.

Yield: 70%.

EXAMPLE 2

Anhydro-2,5-dimethyl-6-methoxy-3-[3-sulphopropyl]-benzoselenazolium hydroxide, Mp. 299°–300° C.

0.01 mol of 2,5-dimethyl-6-methoxybenzoselenazole is mixed with 1.5 ml m-cresol and, after the addition of 0.01 mol of Compound 3, the mixture is heated at 135° C. for 1 hour while being stirred. The melt is then ground finely with propanol and the crystallised quaternary salt is filtered by suction.

Yield: 60%.

EXAMPLE 3

Anhydro-1-[3-sulphopropyl]-quinaldinium hydroxide (Mp. 284° C.) is obtained by heating quinaldine and Compound 5 in an equivalent molar ratio for 1 hour at 125° C. and working up with ethyl acetate, acetone and ethanol, the yield being 30%. In place of Compound 5, Compound 2 can also be used.

EXAMPLE 4

Anhydro-2-methyl-5-phenyl-3-[3-sulphopropyl]-benzoxazolium hydroxide, Mp. 301° C.

(a) By heating 2 g of 2-methyl-5-phenylbenzoaxazole for 3 hours with 2 g of Compound 3 at 140° C. and subsequently grinding it finely with isopropanol.

Yield: 0.8 g.

(b) By the introduction of 2.1 g 2-methyl-5-phenylbenzoxazole into a mixture of 2.4 g of Compound 5 and 1.5 ml m-cresol at 125° C. over a period of 30 minutes, stirring for one hour at 125° C. and working up with ether and ethanol.

Yield: 1.7 g = 51%.

EXAMPLE 5

Anhydro-1,2-dimethyl-5-pyrrolidinosulphonyl-3-[3-sulpho-propyl]-benzimidazolium hydroxide (Mp. 339° C.) is obtained by the reaction of 0.01 mol of 1,2-dimethyl-5-pyrrolidinosulphonylbenzimidazole with 0.01 mol of Compound 5 by heating to 125° C. for 2 hours, and treating the reaction product with boiling methanol, with a 40% yield.

If Compound 6 is used instead of Compound 5, a 50% yield is obtained.

EXAMPLE 6

Anhydro-2-methylthio-3-[3-sulphopropyl]-benzothiazolium hydroxide, Mp. 243°–246° C.

0.01 mol 2-methylthiobenzothiazole is heated with 0.01 mol of Compound 3 with the addition of 1 ml m-cresol for 1.5 hours at 135° C. After cooling, grinding finely with propanol and standing overnight the quaternary salt crystallises.

Yield: 30%.

EXAMPLE 7

Anhydro-2,5-bis-methylthio-3-[3-sulphopropyl]-1,3,4-thiadiazolium hydroxide, Mp. 207°–209° C.

(a) 0.01 mol of 2,5-bis-methylthio-1,3,4-thiadiazole is heated with 0.01 mol of Compound 4 for 40 minutes at 100° C. After cooling, it is worked up with a little propanol.

Yield: 2.7 g = 90%.

(b) Analogous to (a) with Compound 3 instead of Compound 4, with the addition of 2 g of phenol and working up by washing with ether and crystallisation from propanol.

Yield: 33%.

EXAMPLE 8

Anhydro-5-phenyl-5',6'-dimethyl-3-ethyl-3'-[3-sulfobutyl]-oxathiacarbocyanine hydroxide, Mp. 290°–292° C.: 1.8 g of 2,5,6-trimethyl benzothiazole is stirred with 2.3 g of Compound 10 with the addition of 0.5 ml m-cresol for 1 hour at 125° C. The quaternary salt produced is not isolated, but is taken up in 15 ml ethanol and after the addition of 3.4 g of 2-[2-phenyliminoethylidene]-3-ethyl-5-phenylbenzoxazoline, 1 ml triethylamine and 0.3 g acetic anhydride, is converted into the dye by stirring for 1 hour at room temperature. Purification is carried out with ethanol.

Yield: 2 g, maximum absorption: 531 nm (methanol).

We claim:

1. The process for the production of heterocyclic sulfobetaine compound of the formula $$CH_2-\overset{\oplus}{N}=(CH-CH=)_n C-Y \atop \underset{SO_3^{\ominus}}{\overset{X}{|}} \diagdown Z \diagup$$

(III)

in which

X represents an alkylene or alkenylene radical having 1 to 7 carbon atoms

Y represents hydrogen, halogen, an alkyl or alkenyl radical having 1 to 6 carbon atoms, or an alkoxy, alkylthio or mercapto group Z represents the residue required to complete a heterocyclic group comprising at least one 5- or 6-membered heterocyclic ring selected from the group consisting of pyrroline, oxazoline, thiazoline, selenazoline, imidazole, oxazole, thiazole, selenazole, oxadiazole, thiadiazole and pyridine rings, and n represents 0 or 1, by reacting at a temperature of from 80° to 200° C. a heterocyclic compound of the formula

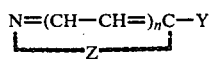  (I)

in which Y, Z and n are as defined above with an isourea compound of the formula

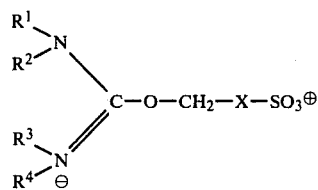  (II)

in which X is as defined above and

R$^1$, R$^2$, R$^3$ and R$^4$ being the same or different represent hydrogen, an alkyl, alkenyl, benzyl or cycloalkyl radical, or two of the substituents R$^1$, R$^2$, R$^3$ and R$^4$ complete together a 5-membered heterocyclic ring containing at least two nitrogen atoms, or R$^1$ and/or R$^3$ represent a phenyl group if the other substituent at the same nitrogen atom (R$^2$, R$^4$) is hydrogen.

2. The process as claimed in claim 1, in which X represents

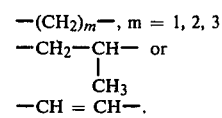

3. The process for the production of anhydro-2,5,6-trimethyl-3-(3-sulfopropyl)-benzothiazolium hydroxide by reacting at a temperature of from 80° to 200° C. 2,5,6-trimethylbenzothiazole with anhydro-O-(3-sulfopropyl)-isouronium hydroxide.

* * * * *